US008664007B2

(12) United States Patent
Klause et al.

(10) Patent No.: US 8,664,007 B2
(45) Date of Patent: Mar. 4, 2014

(54) IMMUNE COMPLEX-SPECIFIC ANTIBODIES FOR INCREASED SENSITIVITY IN IMMUNOASSAY ARRAY TESTS

(75) Inventors: Ursula Klause, Pelβenberg (DE); Helmut Lenz, Tutzing (DE); Christine Markert-Hahn, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 330 days.

(21) Appl. No.: 11/260,938

(22) Filed: Oct. 28, 2005

(65) Prior Publication Data

US 2006/0115907 A1 Jun. 1, 2006

(30) Foreign Application Priority Data

Oct. 30, 2004 (DE) .......................... 10 2004 052 729

(51) Int. Cl.
*G01N 33/543* (2006.01)
(52) U.S. Cl.
CPC .................................... *G01N 33/543* (2013.01)
USPC ............ 436/518; 435/7.1; 435/7.92; 436/524
(58) Field of Classification Search
USPC ............. 435/6, 7.1, 7.92–7.95, 973; 436/501, 436/518, 524, 164, 172
See application file for complete search history.

(56) References Cited

U.S. PATENT DOCUMENTS

| | | | |
|---|---|---|---|
| 4,062,935 | A | 12/1977 | Masson et al. |
| 4,233,286 | A | 11/1980 | Soothill et al. |
| 4,514,508 | A | 4/1985 | Hirschfeld |
| 4,727,037 | A | 2/1988 | Ring |
| 4,795,702 | A | 1/1989 | Blake |
| 5,126,276 | A | 6/1992 | Fish et al. |
| 5,432,099 | A | 7/1995 | Ekins |
| 5,516,635 | A | 5/1996 | Ekins et al. |
| 5,583,054 | A * | 12/1996 | Ito et al. ..................... 436/523 |
| 5,686,562 | A * | 11/1997 | Toukatly et al. ............. 530/324 |
| 5,698,449 | A | 12/1997 | Baumann et al. |
| 5,700,641 | A * | 12/1997 | Salonen .......................... 435/6 |
| 6,489,131 | B1 | 12/2002 | Wehner et al. |
| 2003/0017616 | A1 | 1/2003 | Karl et al. |

FOREIGN PATENT DOCUMENTS

| | | |
|---|---|---|
| DE | 3303793 C2 | 8/1983 |
| EP | 0222146 A2 | 5/1987 |
| EP | 0304202 B1 | 2/1989 |
| EP | 0572845 A1 | 12/1993 |
| EP | 0232165 B1 | 4/1994 |
| EP | 0608370 B1 | 8/1994 |
| EP | 0736176 B1 | 10/1996 |
| EP | 0939313 A2 | 9/1999 |
| EP | 0939319 B1 | 9/1999 |
| EP | 1098198 A1 | 5/2001 |
| EP | 1310794 A2 | 5/2003 |
| JP | 1-22468 | 9/1999 |
| WO | WO 2004/061452 A1 | 7/2004 |
| WO | 2004/081025 A3 | 9/2004 |

OTHER PUBLICATIONS

Robinson et al., Autoantigen microarrays for multiplex characterization of autoantibody responses, Nature Medicine, vol. 8, No. 3, Mar. 2002.*
Diamandis et al., Immunoassay, The Avidin-Biotin System, Chapter 11, pp. 237-255, 1996.*
Mezzasoma et al., Antigen Microarrays for Serodiagnosis of Infectious Diseases, Clinical Chemistry 48:1 pp. 121-130, 2002.*
Robinson et al., Protein Arrays for autoantibody profiling and fine-specificity mapping, Proteomics 2003, 3, 2077-2084.*
Ekins, R. P. et al., "Multianalyte Microspot Immunoassay—Microanalytical "Comact Disk" of the Future," Clin. Chem. 37/11, 1955-1967 (1991).

* cited by examiner

*Primary Examiner* — Gary W Counts
(74) *Attorney, Agent, or Firm* — Roche Diagnostics Operations, Inc.

(57) ABSTRACT

The invention concerns a method for determining antigen-specific antibodies of a particular immunoglobulin class in a sample by means of an immunoassay in an array format in which various binding partners $B_{nx}$ are bound on different discrete areas on a support where $B_{nx}$ in each case contain the various antigens that are able to specifically bind to the antibodies to be detected, by incubating the support with the sample and a binding partner $B_2$ which carries a label and subsequently detecting the label on the respective discrete areas wherein $B_2$ specifically binds antibodies of a certain immunoglobulin class that have been bound in an antigen-specific manner.

10 Claims, No Drawings

IMMUNE COMPLEX-SPECIFIC ANTIBODIES FOR INCREASED SENSITIVITY IN IMMUNOASSAY ARRAY TESTS

RELATED APPLICATIONS

This application claims priority to German patent application DE 102004052729.6 filed Oct. 30, 2004, and to European patent application EP 05023392.3 filed Oct. 26, 2005.

FIELD OF THE INVENTION

The present invention relates to an immunoassay method for an antigen-specific antibody using an array format.

In particular the invention concerns a method for reducing the blank value due to unspecifically bound non-antigen specific antibodies in immunoassays in an array format for detecting antigen-specific antibodies.

BACKGROUND OF THE INVENTION

The immune system of a mammalian organism produces antibodies which are also called immunoglobulins as a response to the introduction of foreign substances. They are used to defend against the foreign substances which are also referred to as antigens. The immunoglobulins can be divided into five different classes. One distinguishes between immunoglobulins of the M, G, A, E, and D classes. These five immunoglobulin classes each differ with respect to the composition of the heavy chain, which is referred to as the $\mu$, $\gamma$, $\alpha$, $\epsilon$, or $\delta$ chain.

Each immunoglobulin class has a different function in the organism. Immunoglobulins of the M class occur when a first contact is made with the antigen, the so-called primary immunization. However, the concentration of these immunoglobulins decreases rapidly as the infection progresses. The immunoglobulins of the G class are firstly slowly formed during a primary immunization and occur in large amounts when there is a second infection with the same antigen. The immunoglobulins of the A class are found on the mucosal surfaces of the organism and are responsible for the defense processes that occur there. The immunoglobulins of the E class are mainly responsible for allergic reactions. The exact function of the immunoglobulins of the D class is hitherto unknown.

The individual immunoglobulin classes occur in blood in very different concentrations. Thus immunoglobulins of the G class (IgG) are the class with the highest occurrence in human serum, being present in a proportion of about 75% which corresponds to a serum content of 8 to 18 mg/ml. The second most frequent immunoglobulin is IgA, whose average serum concentration is 0.9 to 4.5 mg/ml. Immunoglobulins of the M class are present at a concentration of 0.6 to 2.8 mg/ml, and immunoglobulins of class D are present at a concentration of 0.003 to 0.4 mg/ml. IgE antibodies are present in the lowest proportion and only occur at a concentration of 0.02 to 0.05 µg/ml in serum.

For the differential diagnostics of many diseases, it is important to detect antibodies of one or more very particular immunoglobulin classes that are specific for a certain antigen. A satisfactory diagnosis in the case of viral, bacterial and parasitic infection can only be ensured by means of a class-specific antibody detection or by excluding the presence of certain immunoglobulin classes (e.g. detection of IgG and IgA antibodies but no detection of IgM antibodies). This is particularly important for differentiating between fresh or acute infections and older infections as well as to clinically monitor the course of an infection. The class-specific detection of antibodies is especially important for HIV, hepatitis A, hepatitis B, toxoplasmosis, rubella and chlamydia infections. The class-specific detection of antibodies that are specific for a certain antigen is also necessary when determining the titre of protecting antibodies and for checking whether an immunization has been successful.

Various methods are described in the prior art for detecting antibodies of a particular class that are specific for an antigen. Thus antigen-specific antibodies of a particular class are often detected by binding the specific antibody to a solid phase coated with the specific antigen. The immunoglobulins (Ig) that are specific for the antigen and are now bound to the solid phase are detected by binding antibodies that are directed specifically against human Ig of a certain class to the Ig molecules to be detected. The antibodies that are directed against human Ig are provided with a label which is used for the detection. However, such a test procedure is only possible when all unspecific, non-bound Ig is removed by washing before the reaction with the class-specific labelled antibodies directed against human Ig. Thus, for example, when detecting specific IgG molecules in a sample, relatively large amounts (4-20 mg/ml) of unspecific IgGs are present which can absorb sample specifically to different extents and bind unspecifically to the solid phase. If a detection antibody against IgGs is used, these unspecifically bound immunoglobulins will also be recognized and bound. This results in elevated background signals and reduced sensitivity.

One method of reducing these background signals is to modify the solid phase in order to avoid unspecific binding of the immunoglobulins and to use special buffer additives which are also intended to prevent binding of immunoglobulins to the solid phase (examples: HydroGel solid phase (Perkin Elmer), FAST Slides (Schleicher & Schüll), detergents, chaotropic salts). The modifications of the solid phase are laborious and expensive. Furthermore, it has emerged that buffer additives can reduce the reactivity of some antibodies and thus reduce the signals. The background signals induced by unspecifically bound immunoglobulins increase the blank value which makes it more difficult to detect specific antibodies of a certain immunoglobulin class, especially in the case of miniaturized test systems such as immunoassays in an array format which comprise a plurality of specific tests, in some cases in different test formats, in a reaction vessel. Thus, for example, addition of a certain detergent can suppress the unspecific binding of antibodies, but the same detergent can have no effect or even the opposite effect in another test on the same array system.

The use of the coagulation factor C1q, which is a subunit of the first complement component, as a further possibility of reducing background signals in immunoassays is disclosed in EP 0222146 B1. The protein C1q bound to a support is in this case used to selectively remove circulating immune complexes in vivo from the blood by means of extracorporeal immune adsorption in which immune complexes bound to the protein C1q are separated from the body fluids by separating the solid phase. In U.S. Pat. No. 5,698,449 A1, a fragment of C1q is disclosed for selectively removing immune complexes from the blood and for detecting and quantifying the immune complexes. In addition U.S. Pat. No. 4,062,935 A1 describes the addition of rheumatoid factors or C1q to the sample and the binding and quantification of the resulting immune complexes. However, the prior art described here does not show any application for immunoassays in an array format. A characteristic feature of immunoassays in an array format is the solid phase. In such methods the solid phase preferably consists of localized test areas which comprise defined, discrete areas of the solid phase and are preferably spatially separated from other test areas by inert areas. These localized test areas that are defined as spots preferably have a diameter of 10 μm to 1 cm and particularly preferably a diameter of 100-200 μm. Solid phases having several test areas which are also referred to as array systems are preferred. Such array systems are described, for example, in Ekins and Chu (Clin. Chem. 37 (1995), 1955-1967) and in U.S. Pat. Nos. 5,432,099, 5,516,635 and 5,126,276. Array systems have the advantage that several analyte determinations can be carried out simultaneously from one sample. Hence it is possible to apply a plurality of binding partners such as antigen-specific antibodies to the test field. The solid phase of these array systems can be preferably coated with streptavidin or avidin as disclosed in EP 0939319 (Hornauer et al.). Sample components and in particular unspecific IgGs can bind to all these solid phases. In this case it is impossible to use a universal buffer additive to reduce the background signals or it is only possible with a large amount of effort since each individual binding partner requires a very particular buffer additive. Buffer additives which have positive effects in the case of one binding partner may even have adverse effects for other binding partners. It is also very difficult to modify the solid phase for numerous different binding partners. Hence it is impossible to use the above-mentioned methods with a practicable amount of effort to optimize the blank value when several to many different tests are combined on an array solid phase.

Hence the object was to develop a method for carrying out an immunoassay for detecting antigen-specific antibodies in an array format which largely avoids the disadvantages of the prior art and in particular reduces the background signals due to unspecifically-bound immunoglobulins.

SUMMARY OF THE INVENTION

The invention concerns a method for determining antigen-specific antibodies of a particular immunoglobulin class in a sample by means of an immunoassay in an array format in which various binding partners $B_{nx}$ are bound on different discrete areas on a support where $B_{nx}$ in each case contain the various antigens that are able to specifically bind to the antibodies to be detected, by incubating the support with the sample and a binding partner $B_2$ which carries a label and subsequently detecting the label on the respective discrete areas where $B_2$ specifically binds antibodies of a certain immunoglobulin class that have been bound in an antigen-specific manner.

The object of the invention is achieved by the method according to the invention for determining antigen-specific antibodies of a particular immunoglobulin class in a sample by means of an immunoassay in an array format in which various binding partners $B_{nx}$ are bound on different discrete areas on a support where $B_{nx}$ in each case contain the various antigens that are able to specifically bind to the antibodies to be detected, by incubating the support with the sample and a binding partner $B_2$ which carries a label and subsequently detecting the label on the respective discrete areas where $B_2$ specifically binds antibodies of a certain immunoglobulin class that have been bound in an antigen-specific manner.

It surprisingly turned out that the use of $B_2$ according to the invention provides a high sensitivity for antigen-specific antibodies of a certain immunoglobulin class in the spot of the immunoassay in an array format. The use according to the invention of $B_2$ results in the specific binding of mainly antibodies of a certain immunoglobulin class that have been bound in an antigen-specific manner. In this connection, $B_2$ preferably recognizes the antigen-specific antibodies of the immunoassay in an array format that are bound more densely on the spot whereas immunoglobulins that are bound unspecifically to the solid phase are not detected or only to a negligible extent.

DESCRIPTION OF THE INVENTION

The method according to the invention comprises the steps:
providing an array test support which has coated test fields on various discrete areas which each contain the various antigens $B_{nx}$ that are able to specifically bind to the antibodies to be detected,
incubating the test field with the sample which contains the analyte to be detected which is preferably an antigen-specific antibody,
removing excess immunoglobulins,
incubation with the binding partner $B_2$ which carries a label and only specifically binds antibodies of a certain immunoglobulin class that have been bound in an antigen-specific manner, and
detecting the binding partner $B_2$ that is bound to the analyte to be detected.

Another subject matter of the invention is the use of a binding partner $B_2$ which carries a label and specifically binds antibodies of a certain immunoglobulin class that have been bound in an antigen-specific manner, in an immunoassay for detecting antigen-specific antibodies in an array format in order to reduce the blank value.

Antibodies are preferably used as the binding partner $B_2$ in the method according to the invention which specifically bind antibodies of a certain immunoglobulin class that have been bound in an antigen-specific manner. The antibody contains one and preferably several binding sites (also referred to as paratopes, antigen determinants, or combining sites) for the antigen-specific antibody to be determined, i.e., a structure that reacts immunologically specifically with the IgG antibody to be determined. $B_2$ preferably binds aggregated and/or oligomerized specifically bound antibodies of a particular immunoglobulin class which are present in a high density on the spot of the immunoassay in an array format. The antibodies that are bound unspecifically to the solid phase, which are mainly present singly and are loosely distributed, are not detected by $B_2$ or only to a negligible extent.

The use of immune complex-specific antibodies to detect immunoglobulins has already been described many times in the prior art. Immune complex-specific antibodies are rheumatoid factor-like antibodies which preferably bind to aggregated or oligomerized immunoglobulins, but not to single immunoglobulins. EP 1098198 (Berti et al.) concerns a method for the qualitative and quantitative determination of human IgG antibodies in enzyme immunoassays. In this case a monoclonal antibody is used which specifically binds human IgG antibodies to which a specific antigen has bound. New epitopes or binding sites (so-called neo-epitopes) are formed when the antigen binds to the specific antibody. However, in the method described in this document, it is noted that the selective binding to the IgG molecule is associated with loss of signal.

Furthermore, no application for automated systems such as those that are required in particular for immunoassays in an array format is shown. A reduction of the background signal due to antibodies bound unspecifically to the solid phase is not described in this method.

In the method according to the invention, antibodies having a low affinity for binding the antigen-specific antibodies are preferably used for $B_2$. The affinity of an antibody for an epitope is defined as the strength of all non-covalent interactions between the individual antigen-binding site on an antibody and the individual epitope. Antibodies with a low affinity bind weakly and dissociate rapidly whereas high affinity antibodies bind more strongly and remain bound for a longer period. The affinity at a binding site does not always reflect the true strength of an antigen-antibody interaction as, for example, in the case of complex antigens with many repeated antigen determinants and complementary antibodies with several binding sites. The interaction of antigen and an antigen binding site of an antibody (or epitope) at a site increases the probability of a reaction at a second antigen binding site of the same antibody, which can result in a cross-linking of the interaction partners. The strength of such multiple interactions between the multivalent antibody and antigen is referred to as avidity. A high avidity compensates a low affinity as, for example, in the case of the pentameric immunoglobulin IgM. In the method according to the invention, an antibody with a low affinity for the antigen-specific antibody is preferably used which has several, i.e., at least two, preferably at least four, and particularly preferably ten and more paratopes, such as the immunoglobulin IgM or IgG immunoglobulins that are cross-linked with one another. Examples of this are rheumatoid factors which are usually composed of IgM molecules and more rarely also of IgG, IgA, and IgE molecules. Rheumatoid factors react with the Fc part of antibodies.

An average man skilled in the art knows that the value for the affinity of a binding partner, preferably an antibody is determined by the affinity coefficient defined by the model of Langmuir (see P. Uetz, E. Pohl, "Protein-Protein and Protein-DNA Interaktionen" in Wink et al., Molekulare Biotechnologie, Wilea-VCH, 2004). It predicts that the affinity coefficient for a very high affinity is about $10^{-9}$ to $10^{-11}$, for a medium affinity about $10^{-8}$, for a low affinity about $10^{-7}$, and for a very low affinity about $10^{-6}$. The binding partner $B_2$ of the present invention possesses a low affinity, the affinity coefficient is about $10^{-7}$ to $10^{-8}$, this range was determined by a reaction in an analytical study.

If such low affinity antibodies of the binding partner $B_2$ are used, then $B_2$ only recognizes antigen-specific antibodies of the immunoassay in an array format which are bound densely on the spot. Immunoglobulins that are bound unspecifically on the solid phase, which are loosely and non-uniformly distributed, are not detected or only to a negligible extent.

If the specifically-bound antibody to be detected is not present in the spot at a particular density because, for example, the sample is very dilute, it is possible to use an antibody for $B_2$ which specifically binds antibodies to which antigen has been specifically bound. When an antigen is bound to the specific antibody, new epitopes or binding sites (so-called neo-epitopes) are apparently formed. Such antibodies against antigen-bound antibodies are disclosed, for example, in EP 1098198. In the case according to the invention, a neo-epitope can be uncovered by the binding of $B_2$ to the antibody that has been bound in an antigen-specific manner. The neo-epitope-specific bonds are not formed in the case of antibodies that are bound unspecifically to the solid phase, but only in the case of antigen-specific antibodies which are bound to the spot of the immunoassay in an array format.

In the method according to the invention, it is also possible to preferably use antibody fragments for $B_2$ in order to bind the antigen-specific antibodies. Fragmentation of antibodies is known to a person skilled in the art and is carried out by conventional methods. Selection of these antibody fragments according to their usefulness takes place in the same manner as described for complete antibodies. Antibody fragments consist of proteolytically cleaved or recombinantly produced components of an antibody molecule which are able to selectively react with a certain protein. Examples of proteolytically cleaved and/or recombinantly produced fragments are Fab, F(ab')2, Fab', Fv, and single-stranded antibodies (scFv) which contain a V[L] and/or V[H] domain with a peptide linker. The scFv's can be covalently or non-covalently bound, resulting in an antibody with two or more binding sites. The invention also encompasses polyclonal or monoclonal antibodies or other purified preparations of antibodies and recombinantly produced antibodies.

In the method according to the invention, the monoclonal human antibody <h-Agg.-IgG>M3.022.5-IgM-Dig is preferably used for $B_2$. This antibody of the IgM immunoglobulin class has the properties of the general class of rheumatoid antibodies, i.e., it preferably strongly binds antibodies of the immunoglobulin class IgG that have been bound in an antigen-specific manner since it only recognizes the densely packed antigen-specific antibodies on the spot of the immunoassay in an array format. A characteristic feature of the antibody <h-Agg.-IgG>M3.022.5-IgM-Dig is that immunoglobulins causing the blank value that are bound unspecifically to the solid phase of the array that are not specific for the antigen, are not recognized or only to a negligible extent. The use of <h-Agg.-IgG>M3.022.5-IgM-Dig substantially reduces the background signal on the array and sets it at a constant level from sample to sample.

Furthermore, monoclonal antibodies (MAb) of the immunoglobulin class IgM or IgG which are derived from mice, sheep, or other species can also be used for $B_2$. These are known to a person skilled in the art. Polyclonal antibodies (PAb) from various species can also be used provided that in all cases only antibodies that have been bound in an antigen-specific manner are recognized and antibodies that are bound unspecifically to the solid phase are not recognized.

Hence another subject matter of the invention is a method for reducing the blank value in an immunoassay in an array format, characterized in that a binding partner is used as $B_2$ which specifically binds antibodies of a particular immunoglobulin class that have been bound in an antigen-specific manner.

The universal use of the antibody $B_2$ enables several to a large number of different tests to be combined on an array solid phase. A major advantage in this connection is that only a simple and universal buffer composition is required. In Example 2 according to the invention, 2 tests in an indirect test format are combined with a high sensitivity sandwich assay TSH test. TSH (thyroid stimulating hormone) is a hormone which is involved in the regulation of thyroid function. When TSH is detected in a sandwich format, a labelled antibody directed against this antigen is used.

The TSH test makes high demands on the sensitivity; third generation tests can detect concentrations of up to 10-14 M. This high sensitivity is substantially affected by the background signal which should be as low as possible and preferably zero. If the background signals are elevated, it is no longer possible to distinguish low concentrations from the background, resulting in a loss of sensitivity. Thus the TSH test is an ideal measuring quantity for optimizing the blank values.

Antibodies against IgG are used in the test procedure for the binding partner $B_2$ such as the monoclonal antibody <h-IgG PAN>M-R10Z8E9-IgG-Dig. High background signals were measured with this antibody in the TSH test as well as on the control sites of the polystyrene support where no spots had been applied. In addition, the negative control and the negative interfering sample produced even higher background signals with this antibody in the two indirect test formats Jo-1 and Sc170.

The antibody <h-IgG PAN>M-R10Z8E9-IgG-Dig is an example of a commercial anti-human IgG antibody which can be obtained from various companies. For example, the MAb R10Z8E9 from the University of Birmingham recognizes all subclasses of the anti-human IgG. Furthermore, the MAb <h-IgG>, which is directed specifically against all subclasses from the mouse, is obtainable from Pierce, Order No. 37300ZZ, and the MAb <h-IgG>, which recognizes the subclasses IgG 1, 2, and 3 from the mouse, can be obtained from Calbiochem, Order No. 411128.

It was surprisingly found that by using binding partner $B_2$, for example, the antibody according to the invention <h-Agg.-IgG>M3.022.5-IgM-Dig against aggregated IgG, it was possible to reduce unspecific binding to such an extent that background signals were reduced to a satisfactory extent in the highly sensitive TSH sandwich assay as well as in the indirect test formats. The background signals were considerably reduced or no longer present with this binding partner $B_2$, even in the controls "background global", the negative control, and the negative interfering sample.

In the method according to the invention, a plurality of binding partners ($B_{nx}$) are applied to the immunoassay in an array format where $B_{nx}$ in each case contain the different antigens that are able to specifically bind to the antibodies to be detected. This method is also referred to as an indirect test format or antigen-down format. In the method according to the invention, the array preferably consists of a support made of metal, glass, a plastic, or polystyrene. Polystyrene supports are preferably used in the method according to the invention which are known to a person skilled in the art and described, for example, in EP 0939319 (Hornauer et al.).

The binding partners are immobilized on discrete areas of the support, which are defined as test fields that are spatially separated from one another. Test fields comprising one or more spots containing the same binding partner $B_{nx}$ may be preferably present on the support, for example, lines consisting of several identical spots may be formed. Methods for immobilizing the binding partners $B_{nx}$ are familiar to a person skilled in the art and are, for example, disclosed in EP 0939319 (Hornauer et al.). The method described here concerns a method for providing spatially sharply defined test areas for binding assays. For a reliable qualitative and quantitative determination of an analyte it is necessary to be able to produce the test areas of the binding assays in a reproducible manner and with exactly defined amounts of receptor molecules. EP 0939319 (Hornauer et al.) describes that by applying multilayered coatings, it is possible to obtain spatially sharply defined test areas for a binding assay. The coatings comprise applying a precoating on a reagent field of the solid support, washing the precoated support, and applying a second coating comprising receptor molecules that are able to bind to the precoating. The precoating preferably contains a first partner of a high affinity binding pair such as streptavidin, avidin, or biotin as well as analogues, derivatives, and conjugates of the aforementioned substances or antibodies such as anti-mouse antibodies. However, it is also possible to apply molecules as a precoating which are intended to covalently bind to the second coating such as molecules which contain an amine, a sulphide, or a silyl group. Moreover, in EP 0939319 (Hornauer et al.) it was shown that reproducible, homogeneous test spots can be obtained by washing the precoated support with a buffer of a low ionic strength. A second coating containing receptor molecules that are able to bind to the precoating is applied to the washed precoating in the form of spatially defined areas on the reagent field. The receptor molecules preferably contain the second partner of the binding pair which can undergo a high affinity interaction, e.g., an immunological reaction, a streptavidin/avidin interaction, or such like or also a covalent binding with the first partner of the binding pair which is applied as a precoating. Thus, for example, streptavidin or avidin can be applied as a precoating, and the receptor molecule contains a biotin component.

In the present method according to the invention, the sum of all binding partners or antigens to be detected of the entire test fields is defined as $B_{nx}$ ($B_{nx}=B_{n1}+B_{n2}+B_{n3}, \ldots$ etc.). Hence each test field contains a certain type of $B_{nx}$, e.g., test field 1 contains the binding partner or the antigen $B_{n1}$, test field 2 contains the binding partner or antigen $B_{n2}$, test field 3 contains the binding partner or the antigen $B_{n3}$, etc. Thus each test field does not contain a mixture of different antigens $B_{nx}$ but rather a specific type of a binding partner. The specific binding partners can be present in several test fields, e.g., in a row, so that several identical spots may be present. If desired, it is also possible to use mixed spots, i.e., different antigens are contained in a test field. Hence the method according to the invention provides a universal detection method since antigen-specific antibodies that are able to bind specifically with a plurality of binding partners ($B_{nx}$) can be detected with only one binding partner $B_2$.

In the example according to the invention, autoantibodies against the anti-nuclear antigens Jo-1 and Sc170 are, for example, detected. The antibody against Jo-1 is directed against the enzyme histidyl-tRNA synthetase, whereas Sc 170 is a marker for sclerodermia.

Antinuclear antibodies (ANA) are autoantibodies that are directed against various cell components such as, for example, the so-called LE factor in lupus erythematodes visceralis. The specificity of these antinuclear factors (ANF) is very heterogeneous; up to now over 30 antigens that react with ANF are known. These are familiar to a person skilled in the art and are described, for example, in the Biotest—Dictionary of Immunology—on page 145. The method according to the invention can also be used to detect autoantibodies, i.e., typical autoimmune antibodies and also anti-thyroid antigens, anti-islet cell antigens, etc. Furthermore, the method also enables the detection of antibodies against certain pathogens such as toxoplasmosis, rubella, and chlamydia infections.

The binding partner $B_2$ is detected in the method according to the invention by methods known to a person skilled in the art. For this a label is bound to the binding partner $B_2$. All labels familiar to a person skilled in the art which allow a site-specific labelling of the spots can be used. A directly detectable substance is preferably used as the label such as a chemiluminescent, fluorescent, or radioactive substance or a metal sol, latex, or gold particles. Methods for labelling the binding partner $B_2$ are familiar to a person skilled in the art and do not require further elucidation here. The label is detected directly in a known manner by measuring the chemiluminescent, fluorescent, or radioactive substance, or the metal sol, latex, or gold particle and is described in U.S. Pat. No. 0,017,616 (Karl et al.,), U.S. Pat. No. 0,304,202 B1, EP 0736176 B1, EP 0608370 B1 (Ekins et al.), and EP 0939319 (Hornauer et al.).

The label can also be detected indirectly. In this case another binding partner which is itself in turn coupled to a signal-generating group binds specifically to a label of $B_2$, for example, a hapten such as digoxigenin. The signal-generating group, for example, a chemiluminescent, fluorescent, or radioactive substance or an enzyme or gold particle, is detected by methods familiar to a person skilled in the art. An antibody or antibody fragment which specifically binds to the label of $B_2$ can, for example, be used as a further binding partner, for example, an antibody which is directed against digoxigenin or against the hapten.

In the method according to the invention, the binding partner $B_{nx}$ is bound to a solid phase. In this case, $B_{nx}$ can be bound directly to the solid phase. $B_{nx}$ is directly bound to the solid phase by methods known to a person skilled in the art. $B_{nx}$ can also be bound indirectly to the solid phase by means of a specific binding system. In this case, $B_{nx}$ is a conjugate which contains the antigen and a reaction partner of a specific binding system. In this case, a specific binding system is understood as two partners which can specifically react with one another. The binding capability can in this case be based on an immunological reaction or on another specific reaction. Such reaction partners and their use in immunoassays for coating test supports with specific antigens or antibodies are known to a person skilled in the art. A combination of biotin and avidin or biotin and streptavidin is preferably used as a specific binding system. Other preferred combinations are biotin and antibiotin, hapten and antihapten, Fc fragment of an antibody and antibody against this Fc fragment, or carbohydrate and lectin. One of the reaction partners of this specific binding pair is then a part of the conjugate which forms the binding partner $B_{nx}$. The other reaction partner of the specific binding system is bound to the support. The binding of the other reaction partner of the specific binding system to a support material can be carried out using common methods known to a person skilled in the art. In this case, a covalent as well as an adsorptive binding is suitable.

All biological fluids known to a person skilled in the art can be used as samples. Body fluids such as whole blood, blood serum, blood plasma, urine, saliva, liquor, etc. can be preferably used as the sample.

In addition to the sample, the solid phase, and the aforementioned receptors, the test mixtures can contain additives required for the applications such as buffers, salts, detergents, and protein additives such as BSA. The required additives are known to a person skilled in the art or can be found by him in a simple manner.

In addition, the invention concerns a test kit for determining antigen-specific antibodies of a certain immunoglobulin class in a sample by means of an immunoassay in an array format containing a support on which various binding partners $B_{nx}$ are bound on different discrete areas, detection reagents in separate containers as well as the binding partner $B_2$ which carries a label and specifically binds antibodies of a particular immunoglobulin class that have been bound in an antigen-specific manner. The test kit also contains controls and standards and reagents in one or more solutions containing common test additives such as buffers, salts, detergents, etc. known to a person skilled in the art.

The invention is further elucidated by the following examples.

SPECIFIC EMBODIMENTS

Example 1

Production of Monoclonal Mouse IgM Antibodies with Rheumatoid Factor-like Specificity
Immunogen: h-IgG Polymer 10 mg human IgG1 (Sigma Company) were dissolved in 0.6 ml 25 mM bicarbonate buffer pH 9.5. After adding 3.5 µl 12.5% glutardialdehyde solution, it was incubated for 2 hours at room temperature. Subsequently it was cooled in an ice bath, adjusted to pH 8.3 with 50 mM triethanolamine solution pH 8.0, and 0.15 ml freshly prepared sodium boron hydride solution (8 mg boron hydride/ml water) is added. After 2.5 hours at 0° C., the preparation was dialyzed for 16 hours at 4° C. against 10 mM potassium phosphate buffer/0.2 M NaCl, pH 7.5. The dialysate containing IgG polymer was stored in aliquots at −80° C. or used for immunization and for specificity tests in culture supernatants of hybridoma cells.

h-IgG3 polymer was produced in a similar manner starting from human IgG3 (Sigma Company).

Immunization of Mice

Twelve-week old, female Balb/c mice were firstly immunized intraperitoneally with 100 µg h-IgG1 or IgG3 polymer together with the adjuvant CFA (complete Freund's adjuvant). After 8 days a further immunization was carried out with 100 µg of the respective IgG polymer in CFA. Thirteen days after the initial immunization, 200 µg of the respective polymer was administered intraperitoneally without adjuvant; 14 and 15 days after the initial immunization, 100 µg was administered in each case intraperitoneally and intravenously. The fusion was carried out after 16 days.

Production of Hybridoma Clones
Fusion and Cloning

Spleen cells of an immunized mouse were fused with myeloma cells following the method of Galfré, Methods in Enzymology 73, 1981, 3. Approximately $1 \times 10^8$ spleen cells of the immunized mouse were mixed with $2 \times 10^7$ myeloma cells (P3×63-Ag8-653, ATCC CRL 1580) and centrifuged (10 min at 300 g and 4° C.). The cells were then washed once with RPMI-1640 medium without fetal calf serum (FCS) and again centrifuged at 400 g in a 50 ml conical tube. 1 ml PEG (polyethylene glycol, molecular weight 4000, Merck, Darmstadt) was added and mixed by pipetting. After 1 min in a water bath at 37° C., 5 ml RPMI 1640 without FCS was added dropwise, mixed, filled up to 50 ml with medium (RPMI 1640+10% FCS), and subsequently centrifuged. The sedimented cells were taken up in RPMI 1640 medium containing 10% FCS and sown in hypoxanthine-azaserine selection medium (100 mmol/l hypoxanthine, 1 µg/ml azaserine in RPMI 1640+10% FCS). Interleukin 6 (100 U/ml) was added to the medium as a growth factor. After about 10 days, the primary cultures were tested for specific antibody synthesis. Primary cultures which showed a positive reaction with aggregated human IgG1 but no cross-reaction with monomeric IgG were cloned by means of a fluorescence-activated cell sorter in 96-well cell culture plates. Interleukin 6 (100 U/ml) was added to the medium as a growth additive.

The following hybridoma clones were obtained in this manner:

TABLE 1

| MAb name | Immunogen | Subclass specificity |
|---|---|---|
| MAb<h-Agg.-IgG>M-3.022.5-IgM | h-IgG1 polymer | IgG1 > IgG3 > IgG4 > IgG2 |
| MAb<h-Agg.-IgG>M-1.010.2-IgM | h-IgG1 polymer | IgG1 > IgG3 > IgG4 > IgG2 |
| MAb<h-Agg.-IgG>M-1.1.7-IgM | h-IgG3 polymer | IgG1 > IgG3 > IgG2 > IgG4 |

Screening Test for Monoclonal Antibodies having Specificity for Aggregated, human IgG Streptavidin-coated MTP's were coated with biotinylated human IgG1 or IgG3. Afterwards they were incubated with the monoclonal antibody in the cell culture supernatant. Subsequently the bound antibodies were detected in the usual manner using an anti-mouse-IgM-POD (peroxidase) by reaction with a POD substrate.

Determination of the Subclass Specificity Using Human IgG Bound to a Solid Phase In order to determine the specificity of the antibodies in the culture supernatant of the hybridoma cells, MTP's coated with recombinant streptavidin (MicroCoat Company, Order No. 12-K 96 N) were coated with 1 µg/ml biotinylated h-IgG (h-IgG-Bi) of subclass 1 or 2 or 3 or 4 in incubation buffer. Since IgG bound via biotin to a solid phase behaves like aggregated, polymeric IgG, this experimental approach can be used to determine the subclass specificity. For this, 100 µl h-IgG-Bi solution per well was incubated for 60 minutes at room temperature while shaking and subsequently washed 3 times with 0.9% NaCl/0.05% TWEEN 20 (ICI Americas Inc.).

In the next step, 100 µl of the antibody solution to be examined (culture supernatant) was added to a coated well and incubated for 1 hour at room temperature while shaking. After washing 3 times with 0.9% sodium chloride/0.05% TWEEN 20, 100 µl of a POD-labelled (Fab')2 fragment of a polyclonal antibody from the goat against mouse IgM (Dianova Company, Order No. 115-036-075, concentration used 0.16 µg/ml incubation buffer) was added in each case to detect bound antibody from the sample, incubated for 1 hour at room temperature while shaking, and subsequently washed 3 times with 0.9% sodium chloride/0.05% TWEEN 20.

Finally 100 µl/well ABTS substrate (Roche Diagnostics GmbH, Order No. 1684 302) was added, and the absorbance at 405/492 nm was measured after 30 min at room temperature in an MR700 microplate reader from the Dynatech Company.

Incubation Buffer:
40 mM Na phosphate, pH 7.4
200 mM Na tartrate
0.1% TWEEN 20
0.2% bovine serum albumin Determination of the Reactivity/Cross-reaction with Monomeric, Human IgG1

In order to determine the reactivity/cross-reaction with monomeric, non-aggregated h-IgG1, the monoclonal antibody to be examined was preincubated in the test described above with monomeric, non-aggregated IgG1 in increasing concentrations or in excess. If the measured signal remains unchanged at a high level, there is no cross-reaction. If the measured signal decreases, a cross-reaction has occurred.

For this, microtiter plates (MTP's, MicroCoat Company, Order No. 12-K 96 N) coated with recombinant streptavidin were coated with 1 µg/ml biotinylated h-IgG 1 (h-IgG 1-Bi) in incubation buffer. 100 µl of the h-IgG1-Bi solution was used per well and incubated for 60 min at room temperature while shaking and subsequently washed 3 times with 0.9% NaCl/0.05% TWEEN 20.

The monoclonal antibody to be tested for cross-reaction was preincubated with serial concentrations of up to 1 µg/ml monomeric, non-aggregated IgG1. The preincubation takes place in uncoated 96-well MTP's for 1 hour at room temperature while shaking.

In the next step, 100 µl of this solution (antibody+non-aggregated, monomeric IgG1 in excess) was added to a coated well and incubated for 1 hour at room temperature while shaking. After washing 3 times with 0.9% sodium chloride/0.05% TWEEN 20, 100 µl of a POD-labelled (Fab')2 fragment of a polyclonal antibody from the goat against mouse IgM (Dianova Company, Order No. 115-036-075, concentration used 0.16 µg/ml incubation buffer) was added in each case to detect bound antibody from the sample, incubated for 1 hour at room temperature while shaking and subsequently washed 3 times with 0.9% sodium chloride/ 0.05% TWEEN 20.

Finally 100 µl/well ABTS substrate (Roche Diagnostics GmbH, Order No. 1684 302) was added and the absorbance at 405/492 nm was measured after 30 min at room temperature in an MR700 microplate reader from the Dynatech Company.

The monoclonal rheumatoid factor-like binding antibodies that are suitable in the sense of the invention recognize all human IgG subclasses and exhibit less than 10% cross-reaction with monomeric h-IgG in a competition test. If h-IgG1 polymer is used to determine the reactivity, the measured signal is greatly reduced. Table 1 shows the major properties of the monoclonal antibodies that were found.

Fermentation of Hybridoma Clones to Isolate Monoclonal Antibodies

The hybridoma cells that are obtained were sown at a density of $1 \times 10^5$ cells per ml in RPMI 1640 medium containing 10% FCS and propagated for 7 days in a fermenter (Thermodux Company, Wertheim/Main, model MCS-104XL, Order No. 144-050). Average concentrations of 100 µg monoclonal antibody per ml were reached in the culture supernatant.

Isolation of Monoclonal MAb<h-Agg.-IgG>M-3.022.5-IgM

Seventy g finely ground polyethylene glycol 6000 (Merck Company) was added at room temperature to 1 liter culture supernatant containing >50 µg/ml of the fermented monoclonal IgM. The IgM that precipitated after 45 min was sedimented by centrifugation and dissolved in 50 ml Tris buffer (20 mM Tris/0.2 M NaCl/25 mM glycine/2% sucrose, pH 8). IgM was precipitated a second time from this solution using 6.5% polyethylene glycol 6000 and sedimented by centrifugation. This precipitate was dissolved in 5 ml Tris buffer and dialyzed against the same buffer.

The dialysate was centrifuged until clear and chromatographed over a Superose 6 column (Amersham Biosciences Company) having a bed volume of 350 ml. The operating buffer was 75 mM HEPES/0.25 M NaCl/3% sucrose, pH 7.5. The fractions of the IgM peak having a molecular weight of 900 000 were pooled and concentrated by ultrafiltration to 5 mg/ml. The IgM solution was stored in aliquots at −80° C.

Preparation of Biotinylated h-IgG (h-IgG-Bi)

Five mg h-IgG of subclass 1 or 2 or 3 or 4 (Sigma Company) dissolved in 2 ml 0.1 M sodium phosphate buffer, pH 8.3, was admixed with 50 µl of a 2.67 mM solution of biotinylamino-3,6-dioxaoctanylaminocarbonylheptanoic acid-N-hydroxy succinimide ester in dimethyl sulfoxide and stirred for 60 min at 25° C. The ratio of IgG to activated biotin was 1:4. The IgG-Bi that forms was dialyzed at 4° C. against 20 mM potassium phosphate buffer/O. 1 M NaCl/3% sucrose, pH 7.5. The dialyzed IgG-Bi was stored in aliquots at −80° C.

Preparation of MAb<h-Agg.-IgG>M-3.022.5-IgM-digoxigenin (IgM-Dig)

Five mg MAb<h-Agg.-IgG>M-3.022.5-IgM was adjusted to a total volume of 2 ml with 0.1 M sodium phosphate buffer, pH 8.6. Fifty µl of a 1.11 mM solution of digoxigenin-3-O-methyl-carbonyl-ε-aminocaproic acid-N-hydroxysuccinimide ester in dimethyl sulfoxide was added to this solution and subsequently stirred for 60 min at 25° C. The ratio of IgM to activated digoxigenin was 1:10. The IgM-digoxigenin that forms was dialyzed against 20 mM potassium phosphate buffer/0.1 M NaCl/3% sucrose, pH 7.5. The dialyzed IgM-Dig was stored in aliquots at −80° C.

Example 2

A streptavidin coating was applied over the whole area of a test area of about 2.5×6 mm on a black-stained polystyrene support. Lines of identical spots of approximately 20 per line consisting of biotinylated antigens were applied to the test area in an ink-jet procedure; the diameter per spot was about 150 μm. Subsequently the sample was diluted with sample dilution buffer in a ratio of 1:10, and 40 μl of the diluted sample was pipetted manually into the respective test area of the array. The remaining assay processing took place on a laboratory bread board washer-incubator.

The following test-specific reagents were used:
Sample Dilution Buffer:
  50 mM Tris, pH 7.6; 150 mM NaCl; 0.1% detergent (polydocanol); 0.6% BSA; 0.2% preservative (oxypyrion and methylisothiazolone hydrochloride (MIT))
Wash buffer:
  10 mM Tris, 0.01% polydocanol, 0.001% oxypyrion, 0.001% MIT
Samples:
  human sera, positive samples are commercially available; the negative samples are internal donors Native Jo1 and native Sc 170 were used as biotinylated antigens. Autoantibodies against these antinuclear antigens were detected in an indirect test format. 100 μg/ml of the respective biotinylated antigen was used in each spot solution. In addition, the TSH test was also carried out in this example to check the inventive advantages. The TSH test makes the highest demands on the sensitivity of an assay system and is thus the ideal parameter for optimizing the blank value.

Description of the Test Procedure

The samples were incubated for 6 min at 37° C. After aspirating the sample and washing the test field with wash buffer, they were incubated with the binding partner $B_2$, an antibody labelled with digoxin, for 3 min at 37° C. with a subsequent washing step. After incubation with a fluorescently labelled <Dig> antibody for 3 min at 37° C. and subsequently washing and suction drying the test field, the signals were detected by a CCD camera. The samples were diluted 1:10 with the sample dilution buffer for the measurement.

TABLE 2

Test result when using the monoclonal human antibody <h-IgG PAN>M-R10Z8E9-IgG-Dig:

| Spot assay format | MAb<TSH> sandwich | Jo-1 indirect | Sc170 indirect | Background global |
|---|---|---|---|---|
| Negative control | 406 | 2123 | 25 | 226 |
| Negative interfering sample | 293 | 3107 | 59 | 660 |
| Jo-1 positive 9501 | 763 | 26551 | 0 | 272 |
| Sc170 positive 5510 | 161 | 716 | 10654 | 401 |

The signals shown in Table 2 were achieved by using the monoclonal antibody <H IgG PAN>M-R10Z8R9-IgG-Dig. When using this antibody, extremely high background signals were found in the TSH test as well as on sites of the polystyrene support where no spots had been applied ("background global", right column of Table 2). The negative control and the negative interfering sample also showed even higher background signals with this antibody in the two indirect test formats Jo-1 and Sc170. As a result of these very high background signals, it is not possible to measure low concentrations of analyte since low signals of weakly positive samples are super-imposed by the background signal. As a result, the sensitivity of the test using the antibody <H IgG PAN>M-R10Z8R9-IgG-Dig is not adequate for a routine diagnostic laboratory application.

TABLE 3

Test result using the monoclonal human antibody <h-Agg.-IgG>M3.022.5-IgM

| Spot assay format | MAb<TSH> sandwich | Jo-1 indirect | Sc170 indirect | Background global |
|---|---|---|---|---|
| Negative control | 29 | 364 | 7 | 38 |
| Negative interfering sample | 4 | 449 | 21 | 41 |
| Jo-1 positive 9501 | 0 | 28487 | 0 | 74 |
| Sc170 positive 5510 | 0 | 41 | 9623 | 54 |

The signals shown in Table 3 were obtained by using the antibody Mab<h-Agg.-IgG>M3.022.5-IgM. In this experiment the background signal was substantially reduced and was at a uniform level from sample to sample, the sensitivity reached the desired limits. In the sandwich assay (TSH) and the indirect tests (Jo-1 and Sc 170), unspecific binding is no longer detectable or only to a negligible extent in the negative control and the negative interfering sample. Also the background signal "background global" was considerably reduced by this antibody.

What is claimed is:

1. A method for simultaneously detecting multiple antigen-specific antibodies of a particular immunoglobulin class in a sample, the immunoglobulin class selected from the group consisting of IgG, IgA, IgM, IgE, and IgD, the method comprising:
   (a) providing a solid phase support comprising a plurality of different antigens bound to the solid phase support at different discrete test areas,
   (b) incubating the support with the sample and a universal binding partner specific for the selected immunoglobulin class, wherein the universal binding partner recognizes all subclasses of the selected immunoglobulin class specifically bound to the solid phase support, the universal binding partner being coupled to a detectable label, whereby the antigen-specific antibodies bind specifically to their corresponding antigen to form aggregated and/or oligomerized immune complexes in a test area, and the universal binding partner selectively binds to said aggregated and/or oligomerized immune complexes but fails to bind, or binds only to a negligible extent, to antibodies that are unspecifically bound to the solid phase support, and
   (c) detecting the label on the universal binding partner bound specifically to the test areas,
   wherein the method reduces background noise caused by detecting signal from unspecifically bound antibodies.

2. The method of claim 1 wherein the universal binding partner is an antibody.

3. The method of claim 2 wherein the antibody is a neo-epitope-specific antibody.

4. The method of claim 2 wherein the antibody is an antibody having an affinity of about $10^{-7}$ to $10^{-8}$ to the antigen-specific antibody and having at least two paratopes specific for the antigen-specific antibody.

5. The method of claim 2 wherein the antibody is an antibody having an affinity of about $10^{-7}$ to $10^{-8}$ and having at least four paratopes.

6. The method of claim 2 wherein the antibody is an antibody having an affinity of about $10^{-7}$ to $10^{-8}$ and having at least ten paratopes.

7. The method of claim 1 wherein the antigen is bound to the test area by a binding system selected from the group consisting of biotin/streptavidin, biotin/avidin, hapten/antihapten, Fc fragment of an antibody/antibody against the Fc fragment, and carbohydrate/lectin.

8. The method of claim 1 wherein the detectable label is selected from the group consisting of chemiluminescent, fluorescent, and radioactive substances.

9. The method of claim 1, wherein the universal binding partner comprises an antibody fragment.

10. The method of claim 1, wherein the universal binding partner is a monoclonal antibody of the immunoglobulin class IgM or IgG having specificity for aggregated IgG.

* * * * *